(12) United States Patent
Saito et al.

(10) Patent No.: US 7,195,833 B2
(45) Date of Patent: Mar. 27, 2007

(54) SOLID OXIDE ELECTROLYTE WITH ION CONDUCTIVITY ENHANCEMENT BY DISLOCATION

(75) Inventors: Yuji Saito, Palo Alto, CA (US); Friedrich B. Prinz, Woodside, CA (US); Yong-Il Park, Kyungbuk (KR); Ryan O'Hayre, Castle Rock, CO (US)

(73) Assignees: The Board of Trustees of the Leland Stanford Junior University, Palo Alto, CA (US); Honda Giken Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 10/449,709

(22) Filed: May 29, 2003

(65) Prior Publication Data

US 2004/0038106 A1    Feb. 26, 2004

Related U.S. Application Data

(60) Provisional application No. 60/384,378, filed on May 29, 2002, provisional application No. 60/384,380, filed on May 29, 2002.

(51) Int. Cl.
*H01M 8/10* (2006.01)
(52) U.S. Cl. .................... 429/33; 429/30; 428/702; 204/424
(58) Field of Classification Search ................ 429/12, 429/30, 33; 428/688, 689, 702
See application file for complete search history.

(56) References Cited

U.S. PATENT DOCUMENTS

| | | | |
|---|---|---|---|
| 4,069,068 A | 1/1978 | Beyer et al. ................. | 148/1.5 |
| 4,948,680 A * | 8/1990 | Madou et al. ................ | 429/13 |
| 5,063,123 A * | 11/1991 | Ohsuga et al. ............... | 429/38 |
| 5,310,575 A | 5/1994 | Friese et al. ............. | 427/126.3 |
| 5,387,541 A | 2/1995 | Hodge et al. ................. | 437/71 |
| 5,514,904 A * | 5/1996 | Onga et al. .................. | 257/627 |
| 5,731,097 A * | 3/1998 | Miyashita et al. ............ | 429/30 |
| 6,437,375 B1 | 8/2002 | Beaman ...................... | 257/192 |
| 6,465,365 B1 | 10/2002 | Annapragada .............. | 438/763 |

OTHER PUBLICATIONS

F. Prinz et al., "Recovery of dislocation structures in plastically deformed copper and nickel single crystals," ACTA METALL. vol. 30 pp. 821 to 830, 1982.

Harry L. Tuller, "Ionic conduction in nanocrystalline materials," Solid State Ionics 131 (2000) 143-157.

William G. Johnston, "Effect of plastic deformation on the electrical conductivity of silver bromide," Physical Review, vol. 98, No. 6, Jun. 15, 1995.

Joachim Maier, Space charge regions in solid two-phase systems and thei conduction contribution-I. conductance enhancement in the system ionic conductor- 'inert' phase and application on AgCl: $Al_2O_3$ and $AgCl:SiO_2$, J. Phys Chem Solids vol. 46, No. 3, pp. 309-320, 1985.

G. Cochrane et al. "Ionic conductivity and low frequency dispersion in hexagonal silver iodide," J. Phys. Chem Solids, 1971, vol. 32, pp. 2557-2657.

J. M. Dixon et al., "Electrical resistivity of stabilized zirconia of elevated temperatures," Journal of the Electrochemical Society, Apr. 1963.

T. H. Etsell et al., "The electrical properties of solid oxide electrolytes," Chemical Reviews, 1970, vol. 70, No. 3.

Pl Abelard et al., "The electrical conductivity of cubic stabilized zirconia, the results of an IUPAC collaborative study," Pure & Appl. Chem., vol. 67, No. 11, pp. 1891-1904, 1995.

Tomonobu Hata et al., "Yttria-stabilized zirconia (YSZ) heteroepitaxially grown on Si substrates by reactive sputtering," T. Hata et al./Vacuum 59 (2000) 381-389.

J. Will et al., "Fabrication of thin electrolytes for second-generation solid oxide fuel cells," J. will et al./Solid State Ionics 131 (2000) 79-96.

Xia Changrong et al., "Sol-gel synthesis of yttria stabilized zirconia membranes through controlled hydrolysis of zirconium alkoxide," Journal of Membrane Science 162 (1999) 181-188.

Igor Kosacki et al., "Electrical conductivity of nanocrystalline ceria and zirconia thin films," Solid State Ionics 136-137 (2000) 1225-1233.

A. Tschope et al., "Grain size-dependent electrical conductivity of polycrystalline cerium oxide, I, Experiments" Solid State Ionics 139 (2001) 255-265.

A. Tschope et al., "Grain size-dependent electrical conductivity of polycrystalline cerium oxide, II, Space charge model" Solid State Ionics 139 (2001) 267-280.

P. Mondal et al., "Enhanced specific grain boundary conductivity in nanocrystalline $Y_2O_3$-stabilized zirconia," Solid State Ionic 118 (1999) 331-339.

Jean Philibert, "Grain boundary diffusion and oxidation processes," solid State Ionics 117 (1999) 7-11.

Ulrich Brossmann et al., "Oxygen diffusion in ultrafine grained monoclinic $ZrO_2$," Journal of Applied Physics, vol. 85, No. 11, Jun. 1, 1999.

(Continued)

*Primary Examiner*—Patrick Joseph Ryan
*Assistant Examiner*—Julian Mercado
(74) *Attorney, Agent, or Firm*—Lumen Intellectual Property Services

(57) ABSTRACT

Dislocations are fabricated into electrolyte membrane films to increase ion conductivity. Ion and/or electron irradiation causes the growth of vacancy clusters within the thin film and collapsing into Frank dislocation loops that exhibit high ion conductivity. Maximum ion conductivity is accomplished by spatially reorienting the Frank dislocation loops during a following heat-treatment of the membrane. Thereby the dislocation loops form surface-to-surface continuous dislocations along which ions may propagate between membrane surfaces with minimal activation energies. Dislocation densities in the range of $10^8 \sim 10^{14}$ cm/cm$^3$ may be fabricated with conventional irradiation techniques into ceramics such as, for example yttria stabilized zirconia and doped ceria.

11 Claims, 7 Drawing Sheets

OTHER PUBLICATIONS

Hiroyuki Uchida et al., "Effect of ionic conductivity of zirconia electrolytes on the polarization behavior of various cathodes in solid oxide fuel cells," Juournal of the Electrochemical Society, 146 (1) 1-7 (1999).

H. Uchida et. al., "High performance electrodes for medium-temperature solid oxide fuel cells: Activation of La(Sr)CoO$_3$ cathode with highly dispersed Pt metal electrocatalysts," Solid State Ionic 135 (2000) 347-351.

D. Baither et al., "HVEM high-temperature in situ straining experiments on cubic zirconia single crystals," Materials Science and Engineering A233 (1997) 75-87.

"Introduction to Ceramics" by W. David Kingery, H. K. Bowen, Donald R. Uhlmann (Wiley-Interscience; 2nd edition, Apr. 20, 1976) pp. 125-176.

* cited by examiner

SOLID OXIDE ELECTROLYTE WITH ION CONDUCTIVITY ENHANCEMENT BY DISLOCATION

PRIORITY CLAIM

The present invention claims priority to the U.S. provisional application titled "Solid oxide electrolyte with ion conductivity enhancement by dislocation", filed May 29, 2002, Application No. 60/384,378, which is hereby incorporated by reference.

The present invention also claims priority to the U.S. provisional application titled "Sub-micron Electrolyte Thin Film on Nano-Porous Substrate by Oxidation of Metal Film", filed May 29, 2002, Application No. 60/384,380, which is hereby incorporated by reference.

CROSS REFERENCE

The present invention cross references the concurrently filed U.S. application titled "Sub-micron Electrolyte Thin Film on Nano-Porous Substrate by Oxidation of Metal Film" by Yong-il Park, Fritz B. Prinz, Suk-Won Cha, Sang-Joon John Lee & Yuji Saito, Ser. No. 10/449,736, which is hereby incorporated by reference.

FIELD OF INVENTION

The present invention relates generally to electrochemical devices and methods. More particularly, the present invention relates to solid oxide ion conducting electrolyte materials for solid-state ionic devices such as fuel cells and gas sensors, by the use of dislocation.

BACKGROUND

A fuel cell is an electrochemical device that produces electrical current from chemical reactions. The fundamental device includes an ion-conducting electrolyte between two electrodes, backed by fuel and oxidant flow distributors. A catalyst on one electrode promotes separation of ions and electrons at the oxidant side. Only the ions conduct through the electrolyte, and recombine with electrons at the fuel side. The electrons are conducted through an external circuit, thus supplying electrical power. Solid oxide fuel cells (SOFC's) have ionic-conducting metal oxide membranes as their electrolyte layer. The oxygen molecules are split into their respective electrons and oxygen ions at the airside. The oxygen ions propagate through the electrolyte membrane and combine with their electrons and hydrogen molecules into water. A gas sensor has the same basic configuration, and produces electrical current that depends on difference of gas concentration.

Fuel cell operation is increasingly efficient where the well-known electron conductivity of the electrolyte is brought to a minimum and the well-known ionic conductivity of the electrolyte is brought to a maximum. At the same time it is well known that a fuel cell is thermodynamically more efficient at lower temperatures, with lower entropic losses resulting in a higher open cell voltage.

Solid oxide fuel cells [SOFC] have a number of advantages:
No humidity requirement for ion exchange
No water clogging up with generated water
No or less noble metal catalyst
High CO tolerance
Valuable waste heat However, SOFCs have problems. One of the main problems to be overcome is preparation of hermetic seals. With decreasing operating temperature from 1000° C. to 600° C. or less, metal materials can be used for sealing and the problem becomes manageable. Many efforts have been made to decrease operating temperature of SOFCs to below 600° C. despite a large loss of output power. However, this operating temperature is still too high for mobile application.

In particular, an electrolyte layer is needed that may be fabricated in an inexpensive fashion with a configuration that provides for an efficient fuel cell operation at working temperatures of generally less than 500° C. The present invention addresses also these needs.

SUMMARY

The present invention provides a solid oxide electrolyte thin film with dislocations, which penetrate (pass through) electrolyte from a top surface to bottom surface. The present invention adopts preferably ion irradiation in combination with a heat treatment for fabricating electrolyte thin films. One preferred embodiment of the present invention is based on:

1. Conventional ion conducting materials, such as, but not limited to, Yttria stabilized zirconia or doped ceria prepared as an electrolyte.
2. Dislocations that are introduced into electrolyte materials, preferably by the use of high-energy electron irradiation and/or ion irradiation.
3. Shape and direction of the dislocations are modified by heat treatment.

Some of the advantages of the present invention over existing devices and methods include:

1. High ionic conductivity enabling high power density/efficiency fuel cells and high-sensitive gas sensors.
2. Low Temperature operation solving problems caused by difference of thermal expansion coefficient between electrode and electrolyte materials, and also enabling free device design by enlarged availability of materials including metals and polymers.

DETAILED DESCRIPTION

Ceramics with naturally high ionic conductivity such as yttria stabilized zirconia [YSZ] and doped ceria such as samarium doped ceria [SDC] are preferred materials for electrolyte materials. Fluid impermeable thin film layers may-be fabricated from such ceramics in a single-crystal, polycrystalline and eventually amorphous condition. Dislocations may be fabricated in single-crystal and/or polycrystalline ceramics. Generally, dislocations may be fabricated by plastic deformation, rapid cooling, or irradiation with ions, electrons or neutrons.

Plastic deformation may yield dislocation densities of up to $10^{10}$ cm/cm$^3$. However, plastic deformation in ceramics can only be done at high temperatures. In YSZ, plastic deformation will occur at appreciably high rates only at temperatures above 1000° C. Plastic deformation at elevated temperatures requires complex fabrication steps especially with films thicknesses that are relevant for efficient electrolyte membranes.

Alternatively to plastic deformation, dislocations can also be introduced through rapid cooling or quenching. In this process, ceramic membranes may be heated to temperatures above 1000° C. and followed by a rapidly cooling. The heating and cooling sequence will freeze in a high density of vacancies into the atomic lattice structure. For best results it is desirable to perform the cooling process as short as possible. Short cooling steps with a high temperature gradient induce significant mechanical strain into the ceramics with a high likelihood of cracking. In an electrolyte membrane, cracks need to be avoided for preventing fluid permeation.

Irradiation is the preferred method of fabricating thin films with dislocation densities of $10^{12}$ cm/cm$^3$ and higher. Ceramics may be irradiated with ions, electrons and/or neutrons. Neutron irradiation may result in residual radioactive isotopes. Ion irradiation and electron irradiation to the contrary, are environmentally safe, simple and inexpensive to accomplish with readily available equipment.

Ion/electron irradiation causes the growth of vacancy clusters within an irradiation depth of the ceramics. Once the vacancy clusters reach a critical size, the surrounding atomic lattice structure collapses and the vacancy clusters are transformed into well-known Frank dislocation loops. In a heat treatment process following the irradiation, the ceramic is heated up to a temperature and held there for a time period during which the Frank dislocation loops spatially reorient themselves and form continuous dislocations. The heat treatment parameters are adjusted in a well-known fashion to keep recombination of the dislocation loops to but a minimum.

Figure 1:
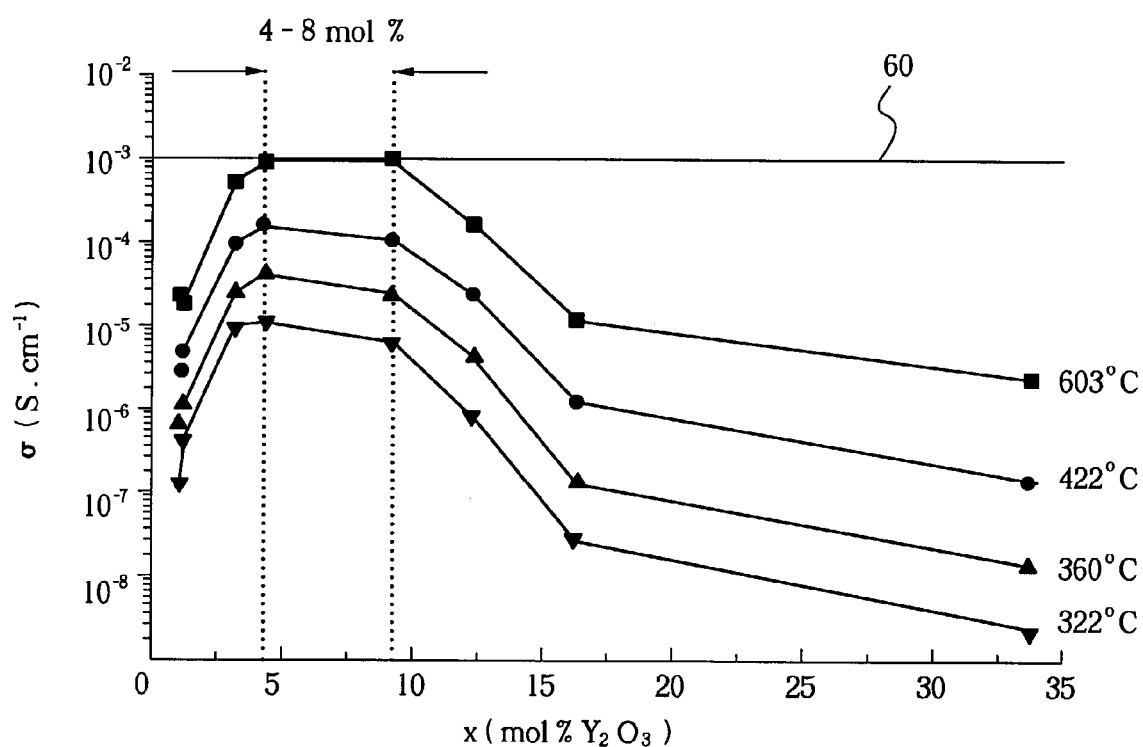
FIG. 1 illustrates exemplary isothermal curves for ionic conductivity as a function mol % $Y_2O_3$ for YSZ.

A preferred ceramic for irradiation fabricated continuous dislocations is YSZ. The natural ionic conductivity σ of YSZ depends on its content of yttrium oxide $Y_2O_3$. As illustrated by the isothermal lines in FIG. 1, the natural ionic conductivity σ is at a maximum in the range of 4~8 mol% $Y_2O_3$. The isothermal lines mark exemplary temperatures of the YSZ material. A maximum natural ionic conductivity increasingly centers around 4 mol% $Y_2O_3$ as the temperature of the YSZ material is reduced. The natural ionic conductivity σ depicted in FIG. 1 is substantially without dislocations.

Figure 3:
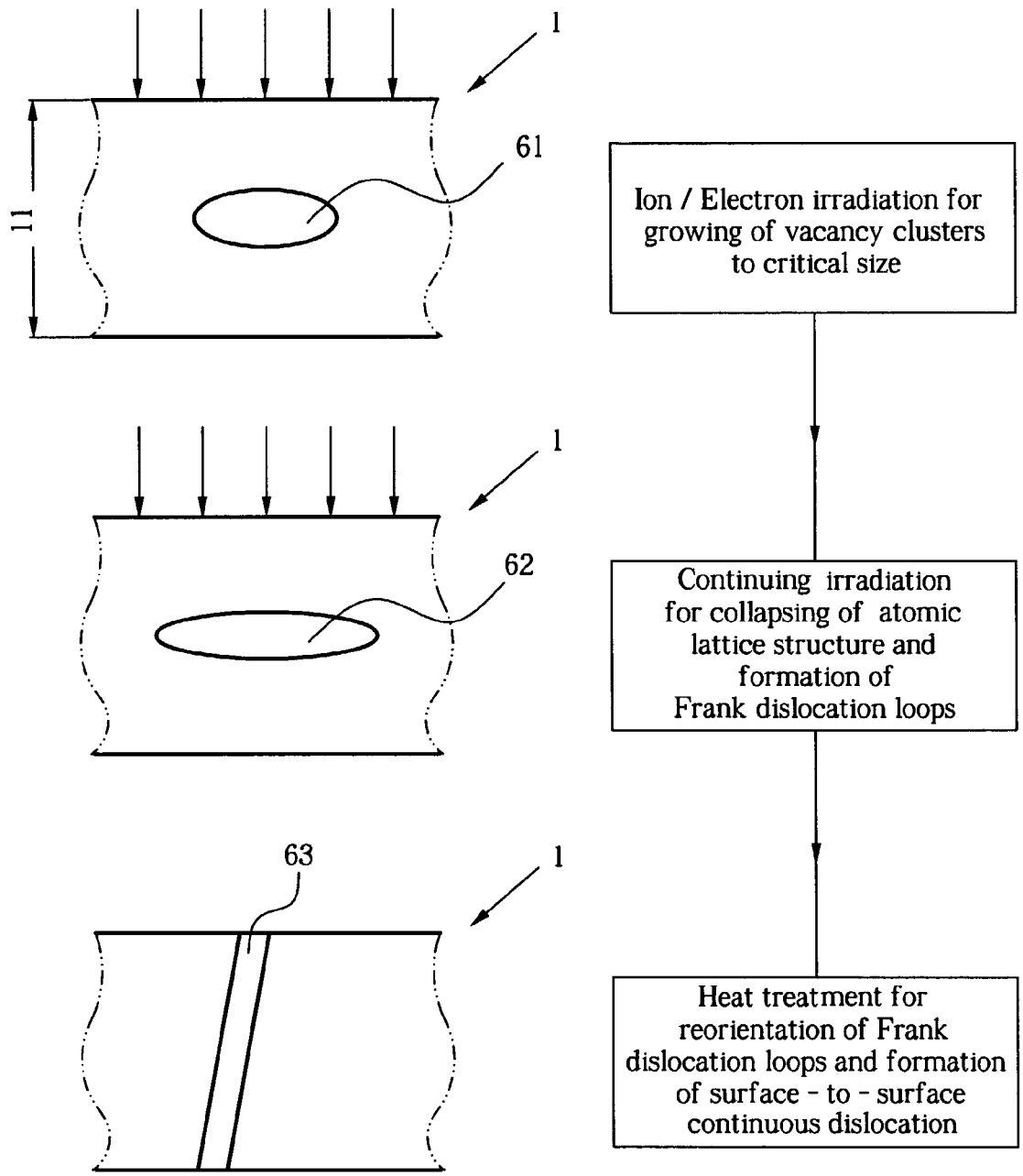
FIG. 3 schematically depicts the steps for fabrication of a film with surface to surface dislocations with associated block diagram.

Reference line 60 is an ionic conductivity benchmark of about $10^{-3}$ for a 500 nm thick YSZ thin film 1 (see FIG. 3). For more details about the relation between ionic conductivity, thin film thickness and total ionic resistance of a thin film please refer to the cross referenced and concurrently filed application for "Sub-micron Electrolyte Thin Film on Nano-Porous Substrate by Oxidation of Metal Film".

Figure 2:
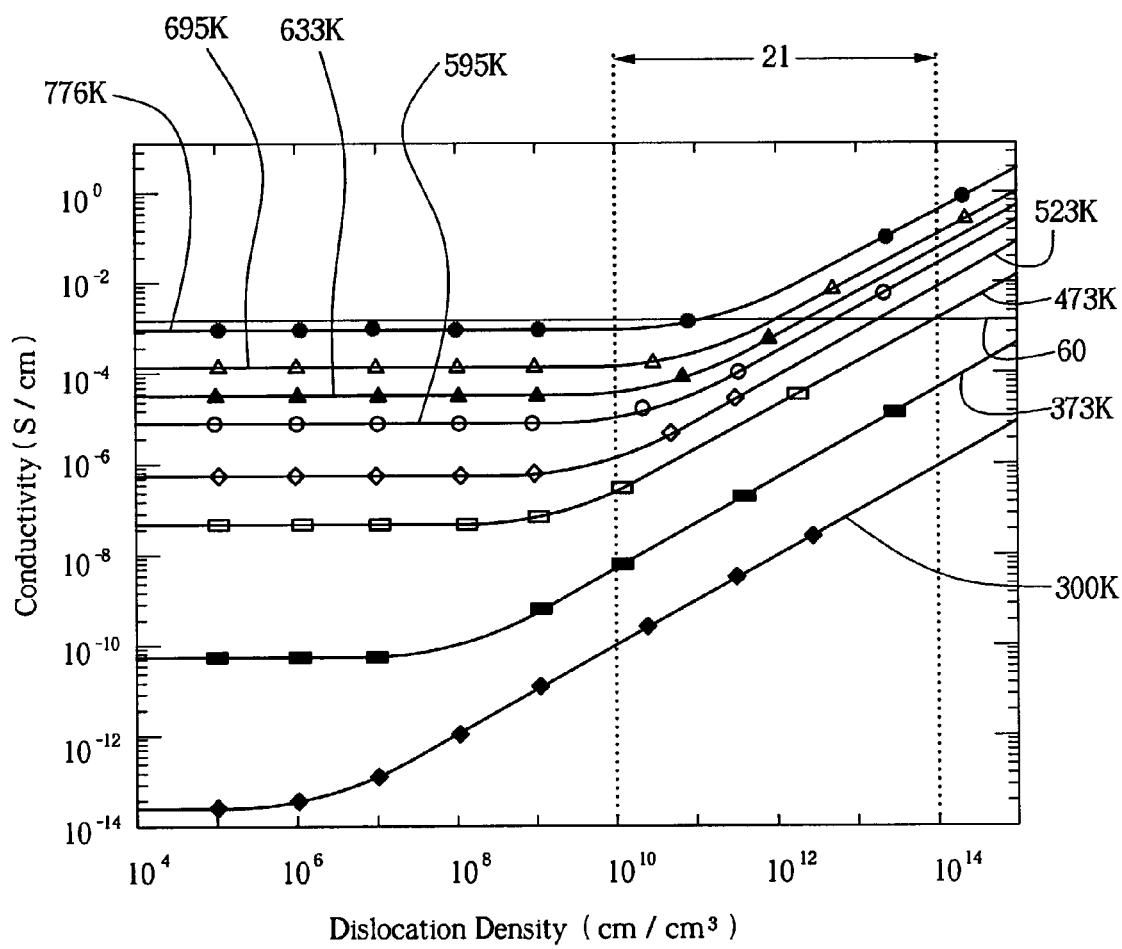
FIG. 2 depicts exemplary isothermal curves for ionic conductivity as a function of dislocation density.

FIG. 2 shows the ionic conductivity of YSZ with 8 mol % $Y_2O_3$ [8YSZ] in dependence of dislocation density for exemplary temperatures. The exemplary temperatures encompass approximately a preferred operational temperature range for an electrolyte membrane in a fuel cell. It is desirable to have a fuel cell operating below a maximum temperature limit of about 500° C., to reduce well-known constrictive efforts for operating the fuel cell. Such constructive efforts may include, for example, the selection of high temperature materials for structural parts and seals and/or design features to comply to thermal expansion, heat dissipation, heat transfer and so forth.

As shown in FIG. 2, within the dislocation density range 21 between $10^{10}$ and $10^{14}$ cm/cm$^3$ ion conductivity is substantially reduced. Introduction of continuous dislocations may increase ion conductivity between about 2 magnitudes in the high temperature region to about 8 magnitudes in the low temperature region. Thus, as operational temperatures of fuel cells and gas sensors decrease, continuous dislocations gain significance for efficient electrolyte membrane fabrication.

Ion conductivity in a solid material containing dislocations is estimated as follows: the dislocation densities are estimated for dislocation pipes defined by $\rho_{pipe}$ whereby units are length of dislocation per volume, or [mm-2]. Assuming the dislocations are oriented directly through the thickness of material, then the area fraction for conduction via dislocation is the same as the volume fraction of dislocation, which is:

$$f_{pipe} = \rho_{pipe} * \pi b^2$$

This assumes that each dislocation extends over a spatial area given by $\pi b^2$, where b is the burgers vector for the dislocation, usually around 1–2 atoms large. The total conductivity of the sample is then calculated using a rule-of-mixtures argument. Basically, the total conductivity is given as the sum of the conductivity of the bulk material weighted by the volume fraction of bulk material, plus the conductivity of the dislocation pipes weighted by the volume fraction of the dislocation pipes.

The final assumption is that the conductivity in the dislocations is enhanced compared to the conductivity in the bulk. The dislocation enhanced conductivity is due to a decrease in the activation energy (Ea) for conduction in the vicinity of the dislocation pipe. For YSZ this is because around dislocations, lattice is dilated and bonding strength between oxygen and Zr is weaker. Weaker bonding strength in turn results in lower migration (activation) energy of oxygen ion from oxygen site to oxygen vacancy. The activation energy in a dislocation pipe is about [½] of the bulk material's activation energy:

$$\sigma_{bulk} = Ae^{-Ea/kT} \sigma_{pipe} = Ae^{-Ea/2kT}$$

FIG. 3 illustrates the stages involved in the fabrication of continuous dislocations. In a first stage, a thin film 1 previously fabricated with a predetermined thickness 11 is exposed to ion irradiation or electron irradiation. The thickness 11 is selected in conjunction with irradiation parameters such that ions impinging at one surface may propagate and dissipate across the thickness 11. For example, a YSZ thin film may be fabricated with a thickness of about 140 nm. For details about fabrication of a substantially fluid impermeable YSZ thin film it is referred to the concurrently filed and cross-referenced application titled "Sub-micron Electrolyte Thin Film on Nano-Porous Substrate by Oxidation of Metal Film".

The thickness 11 is selected for exemplary irradiation parameters of 5×10$^{15}$ ions/cm$^2$Xe$^{3+}$@ 450 kV resulting in an approximate dislocation density of 10$^{12}$ cm/cm$^3$. During the first stage, vacancy clusters 61 begin to form within the crystalline structure of the thin film 1. As the irradiation continues, the vacancy clusters 61 grow to a critical size.

Other ions such as Argon ions may be used besides Xenon ions. The use of Xenon ions conforms to a well-known Transmission Electron Microscope (TEM) observation. The use of Argon ions to the contrary results in lower dislocation density but deeper penetration, because Ar ion is smaller and lighter than Xe. The use of electrons for irradiation provides much deeper penetration because electrons are much smaller than ions. Penetration depth may be estimated in a well-known fashion such as with a commercially available software "SRIM-2000.40" from IBM. For example, maximum penetration depth in YSZ estimated for 450 keV Ar ion irradiation may be about 340 nm. Irradiation intensities are preferably kept to a maximum for maximum penetration depth and higher dislocation density. As may be well appreciated by anyone skilled in the art, irradiation intensities are limited to levels at which structural damage to the thin film 1 is substantially avoided. In case, a thin film 1 may be accessed for irradiation from both sides 12, 13, the maximum penetration depth may be doubled.

At and beyond critical size and while irradiation continuous, the surrounding atomic lattice structure collapses resulting in a transformation of the vacancy clusters 61 into well-known Frank dislocation loops 62. During that second stage, the dipoles of the Frank dislocation loops 62 are at arbitrary positions within the thin film 1. Ionic conductivity may be improved by sole irradiation where Frank dislocation loops are formed in arbitrary orientation.

Figure 5:
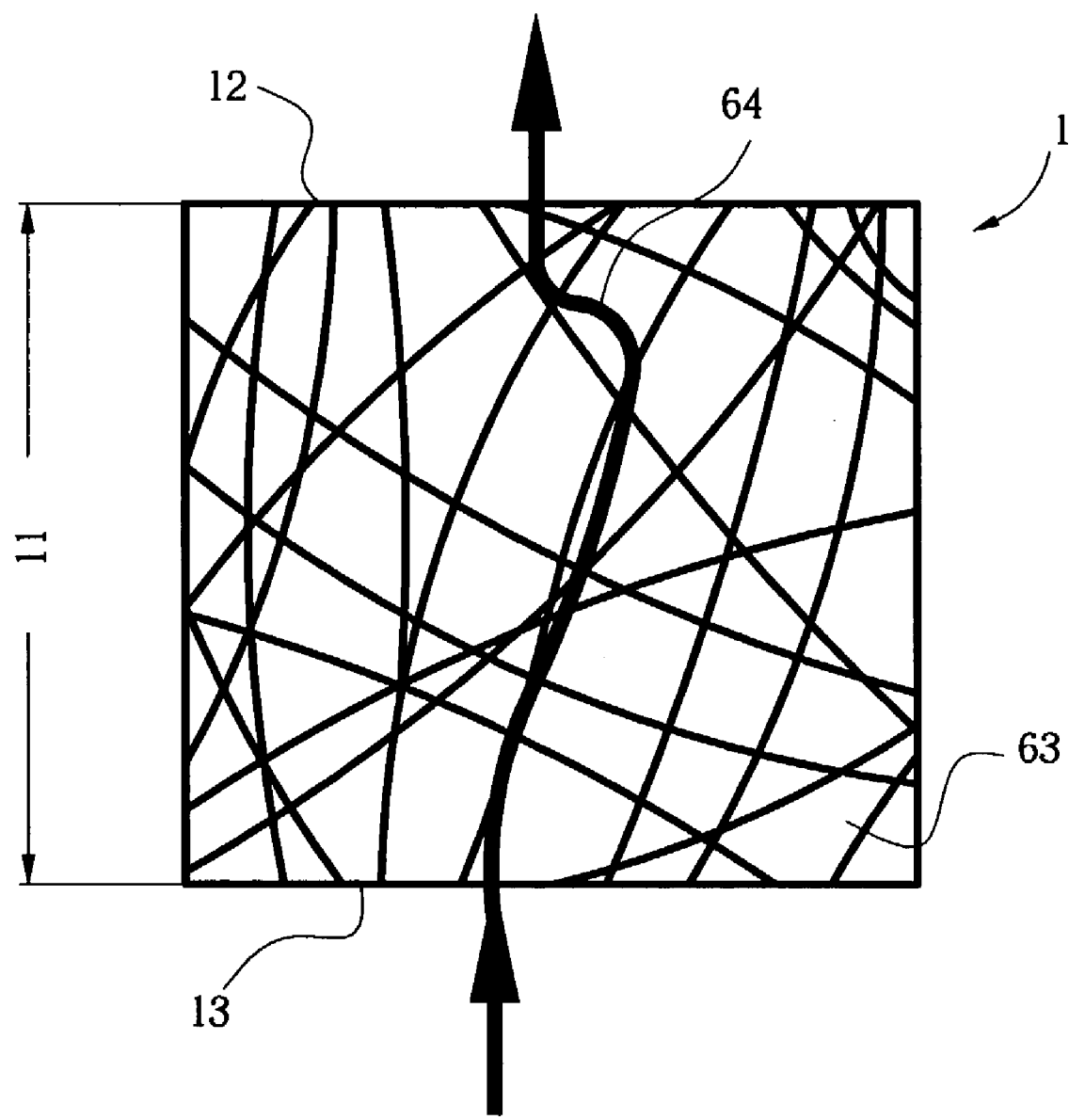
FIG. 5 schematically illustrates the function of a surface to surface dislocation as an ion path.

Ionic conductivity may be brought to maximum levels for a given dislocation density, where the Frank dislocation loops are spatially reoriented such that both dipoles of the dislocation loops coincide with top and bottom surfaces 12, 13 (see FIG. 5). In that way, continuous surface-to-surface dislocations 63 are formed along which ions may propagate between the surfaces 12, 13 with minimal activation energies.

The Frank dislocation loops are spatially reorientated after completion of the irradiation during a separate heat treatment of the thin film 1. For the case of an YSZ thin film 1, the heat treatment may include an exposure to about 800° C. for about 3 hr. The temperature is selected to initiate growth and spatial reorientation of Frank dislocation loops 62 without substantially reducing the dislocation density due to undesired recombination of the dislocation loops. At the end of the heat treatment, the sample is gradually cooled off to prevent the formation of cracks.

Figure 4:
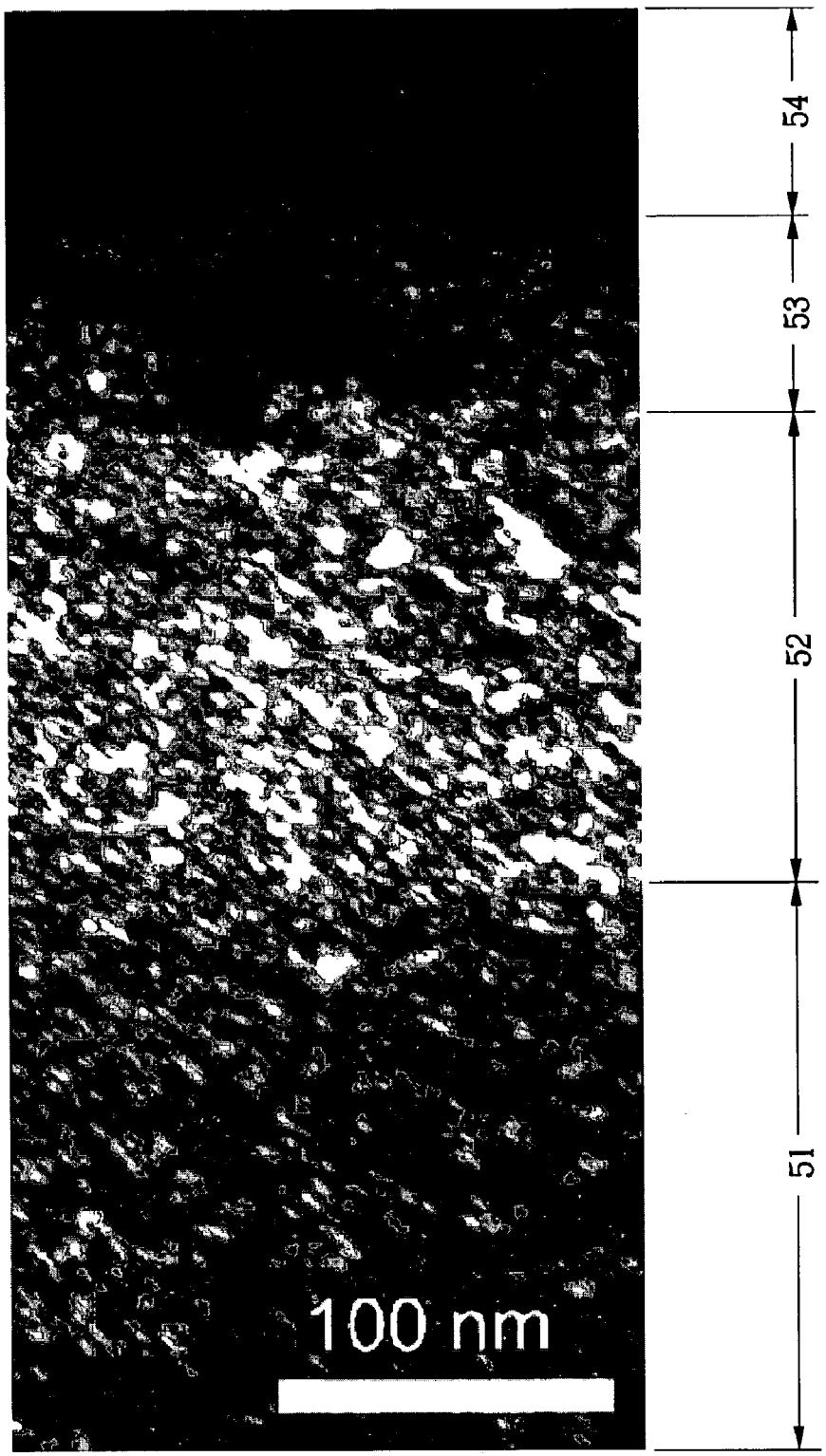
FIG. 4 is an enlarged cross section photograph of a layer structure including a layer having dislocations.

FIG. 4 shows an enlarged TEM photograph of a YSZ multilayer cross section with a platinum layer 54 on top of a gold layer 53 on top of an irradiated YSZ layer 52 on top of a substantially irradiation free YSZ bulk layer 51. The white areas within layer 52 represent dislocations with a dislocation density of about $10^{12}$ cm/cm$^3$. The sample of FIG. 4 has gold and platinum layers 53, 54 on top of the irradiated layer 52. Layers 53, 54 are deposited after irradiation for sample preparation. Also for purposes of sample preparation, the irradiated layer 52 has been fabricated into a bulk layer of which an irradiation unaffected portion 51 is visible in FIG. 4. The Frank dislocation loops, visible as white areas within layer 52 are not spatially reoriented. The sample of FIG. 4 is for the sole purpose of observation.

FIG. 5 schematically illustrates the effect of continuous surface-to-surface dislocations on ion propagation from one thin film surface 13 to the opposite surface 12.

Figure 6:
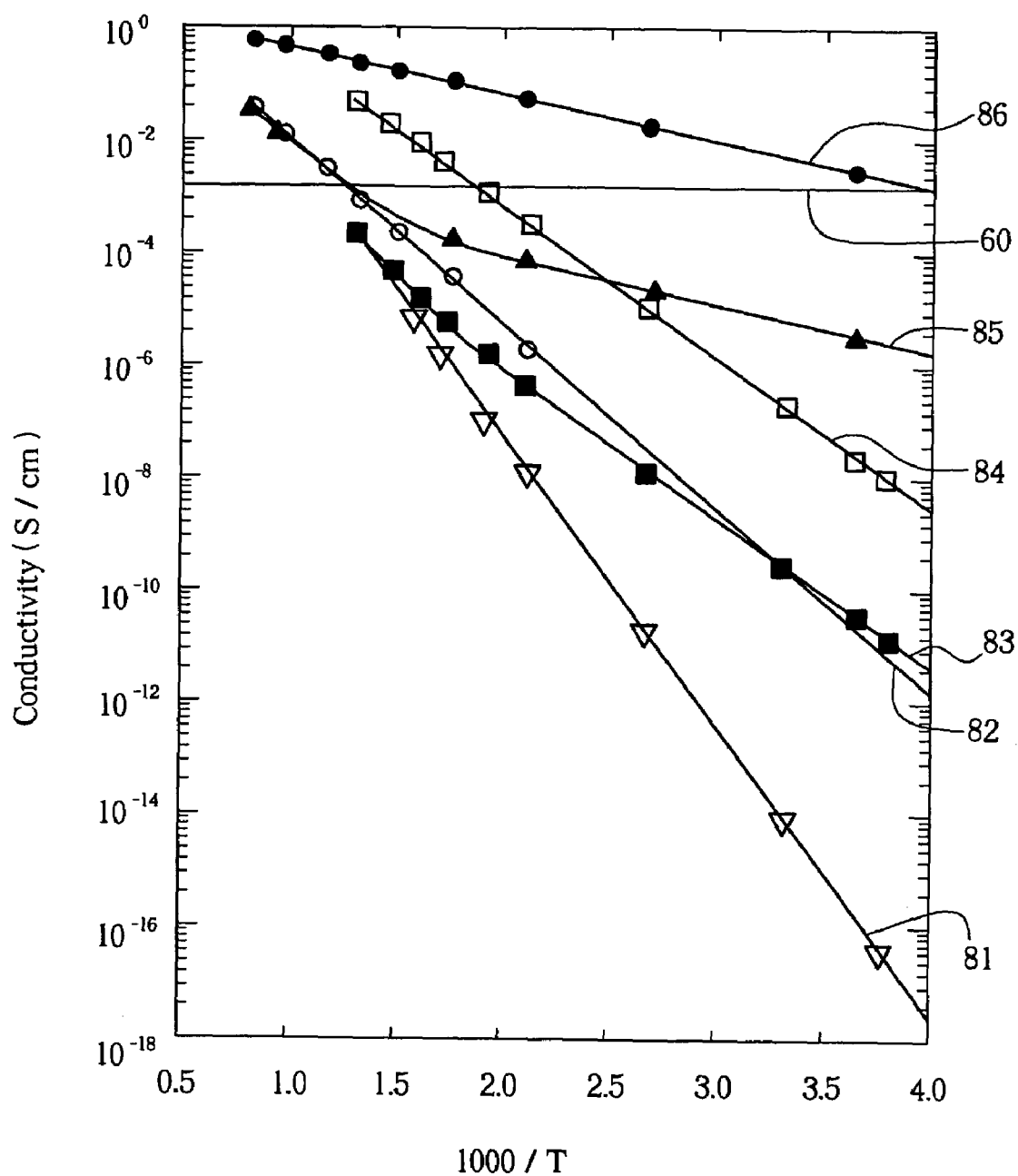
FIG. 6 shows estimated ionic conductivity as a function of temperature for YSZ and Sm-doped ceria at exemplary dislocation densities.

Besides YSZ, SDC is a preferred ceramic material for electrolyte membranes. An SDC may have, for example the chemical formula $Sm_{0.2}Ce_{0.8}O_{1.9}$ [20SDC]. FIG. 6 depicts estimated conductivities as a function of temperature for natural 8YSZ (curve 81) and 20SDC (curve 83) as well as 8YSZ with dislocation densities of $10^{11}$ cm/cm$^3$ (curve 82) and $10^{14}$ cm/cm$^3$ (curve 84) and 20SDC with dislocation densities of $10^{11}$ cm/cm$^3$ (curve 85) and $10^{14}$ cm/cm$^3$ (curve 86).

Figure 7:
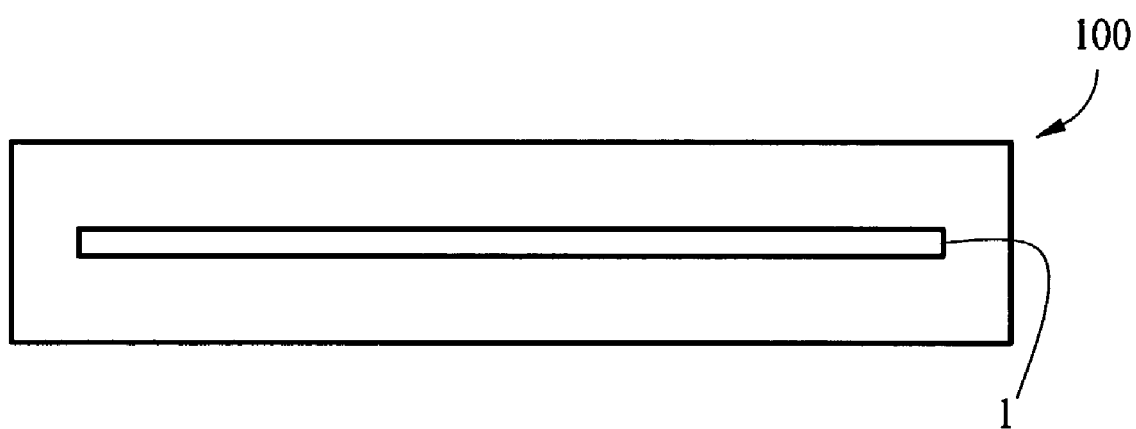
FIG. 7 shows a device having a thin film with dislocations in accordance with the present invention.

FIG. 7 shows a device 100 having a thin film 1 with dislocations in accordance with the present invention. The device 100 may be a fuel cell or a gas sensor.

It will be clear to a person of average skill in the art that the above preferred embodiment may be altered in many ways without departing from the scope of the invention. For example, other fluorite materials, such as, but not limited to, Ca stabilized zirconia and Sc stabilized zirconia may be adopted as an electrolyte material. Also, well-known Perovskite ion conducting materials may be adopted as an electrolyte material.

Accordingly, the scope of the invention described in the specification above is set forth by the following claims and their legal equivalent:

What is claimed is:

1. An ion conducting oxide layer comprising dislocations with a density of at least $10^{10}$ cm/cm$^3$,
   wherein said dislocations are substantially continuously extending between a top surface and a bottom surface of said layer.

2. The layer of claim 1 having a thickness of 350 nm or less.

3. The layer of claim 2 having an ionic conductivity of at least $10^{-6}$ S/cm at a temperature of 200° C.

4. The layer of claim 1 being of YSZ.

5. The layer of claim 1 being of Sm-doped ceria.

6. The layer of claim 5 having an ionic conductivity of at least $5 \times 10^{-4}$ S/cm at a temperature of 200° C.

7. The layer of claim 1 being an electrolyte membrane of a fuel cell.

8. The layer of claim 1, being an electrolyte membrane of a gas sensor.

9. The ion conducting oxide layer of claim 1, wherein the dislocation density is at least $10^{11}$ cm/cm$^3$.

10. The ion conducting oxide layer of claim 1, wherein the dislocation density is at least $10^{12}$ cm/cm$^3$.

11. The ion conducting oxide layer of claim 1, wherein the dislocation density is at least $10^{14}$ cm/cm$^3$.

* * * * *